US006547711B2

(12) United States Patent
Facciotti

(10) Patent No.: US 6,547,711 B2
(45) Date of Patent: Apr. 15, 2003

(54) PRODUCTION OF IMPROVED RAPESEED EXHIBITING YELLOW-SEED COAT

(75) Inventor: Daniel Facciotti, Davis, CA (US)

(73) Assignee: Calgene LLC, Davis, CA (US)

(*) Notice: Subject to any disclaimer, the term of this patent is extended or adjusted under 35 U.S.C. 154(b) by 0 days.

(21) Appl. No.: 10/087,976

(22) Filed: Mar. 5, 2002

(65) Prior Publication Data

US 2002/0124283 A1 Sep. 5, 2002

Related U.S. Application Data

(63) Continuation of application No. 09/072,331, filed on May 4, 1998, now Pat. No. 6,380,466.
(60) Provisional application No. 60/045,866, filed on May 8, 1997.

(51) Int. Cl.$^7$ ............................................... C07C 57/00
(52) U.S. Cl. ........................ 584/227; 554/224; 426/622
(58) Field of Search ............................... 584/224, 227; 426/622

(56) References Cited

U.S. PATENT DOCUMENTS

| 5,276,264 A | 1/1994 | Heaton et al. |
| 5,387,758 A | 2/1995 | Wong et al. |
| 5,545,821 A | 8/1996 | Wong et al. |
| 5,668,299 A | 9/1997 | Debonte et al. |

FOREIGN PATENT DOCUMENTS

| CN | 1108874 A | 9/1995 |

OTHER PUBLICATIONS

Ahmed et al., "Inheritance of Seed Coat Color in *Brassica campestris*L. Variety Toria", *Crop Science*, vol. 11:309–310 (1971).
Chauhan et al., Abstract XP–002075662.
Chauhan et al., Abstract XP–002075663.
Chauhan et al., "Genetics of Oil Content in Yellow Seeded Indian Mustard (*Brassica juncea*)", *Cruciferae Newsletter*, Department of Genetics & Plant Breeding, N.D. University of Agriculture & Technology, pp. 80–83 (1996).
Chen et al., Abstract XP–002075661.
Chen et al., "Inheritance of Seed Colour in *Brassica campestris*L. and Breeding for Yellow–Seeded *B. napus* L.", *Euphytica*, 59:157–163 (1992).
Daun et al., "Quality of Yellow and Dark Seeds in *Brassica campestris* Canola Varieties Candle and Tobin", *JAOCS*, vol. 65(1):122–126 (1988).
Derwent Publications, Abstract XP–002075667.
International Search Report, PCT/US98/09275 (1998).
Jain et al., "Evaluation of Protoclonal Variation Versus Chemically Induced Mutagenesis in *Brassica napus* L.", *Current Science*, vol. 58(4):176–180 (1989).
Shirzadegan et al., "Inheritance of Seed Color in *Brassica napus* L.", *Z. Pflanzenzüchtg.*, vol. 96:140–146 (1986).
Swanson et al., Abstract XP–002075666.
Swanson et al., "Haploid Transformation in *Brassica napus* Using an Octopine–Producing Strain of *Agrobacterium tumefaciens*", *Theoretical and Applied Genetics*, vol. 78(4):831–835 (1989).
Upadhyay et al., Abstract XP–002075664.
Upadhyay et al., Abstract, "Molecular Mapping and Character Tagging in Mustard (*Brassica juncea*) II. Association of RFLP Markers with Seed Coat Colour and Quantitative Traits", *Journal of Plant Biochemistry & Biotechnology*, vol. 5:17–22 (1996).
Van Deynze et al., "Temperature Effects on Seed Color in Black– and Yellow–Seeded Rapeseed", *Canadian Journal of Plant Science*, vol. 73:383–387 (1993).
Van Deynze et al., "The Inheritance of Seed Colour and Vernalization Requirement in *Brassica napus* Using Doubled Haploid Populations", *Euphytica*, vol. 74:77–83 (1994).
Verma et al., Abstract XP–002075665.
Verma et al., Abstract, Mutation in Seed–Coat Colour in Indian Mustard, *The Indian Journal of Agricultural Sciences*, vol. 50(7):545–548 (1980).

*Primary Examiner*—Deborah D. Carr

(57) ABSTRACT

Rapeseed in plants producing rapeseed which have a yellow-seed coat are provided. The yellow-seed coat is controlled by a single locus mutation. Plants from the rapeseed are useful for transferring the trait into elite lines of canola.

72 Claims, No Drawings

PRODUCTION OF IMPROVED RAPESEED EXHIBITING YELLOW-SEED COAT

CROSS-REFERENCE TO RELATED APPLICATIONS

This application is a continuation of U.S. application Ser. No. 09/072,331, filed May 4, 1998, now U.S. Pat. No. 6,380,466, which application claims the benefit of U.S. Provisional Application Ser. No. 60/045,866, filed May 8, 1997, each of which application is herein incorporated in its entirety by reference.

FIELD OF THE INVENTION

This application relates to improved oilseed Brassica plants and the seeds obtained from these plants, wherein such seeds have decreased fiber and increased oil and protein content. This invention also relates to methods for decreasing fiber content and increasing seed oil and protein levels in seeds from oilseed Brassica plants.

BACKGROUND OF THE INVENTION

The term rapeseed is used to refer to a number of oilseed crop plant species within the genus brassica, including *B. napus*, *B. rapa* (syn. campestris), *B. juncea* and B. *carinata*. Spring and winter lines have evolved for *B. napus* and *B. rapa*, while only spring varieties of *B. juncea* are known. *B. napus* winter varieties are grown predominantly in northern Europe, China, and the northwest United States, whereas spring varieties predominate in Canada, northwest China, Denmark, and parts of Sweden. *B. rapa* has a shorter growing season than *B. napus* and this trait makes the spring varieties of this species suitable for the more severe climates of Sweden, Finland and Western Canada. *B. juncea* is grown extensively on the Indian subcontinent, while *B. carinata* is grown primarily in Ethiopia.

The taxonomic structure among members of the Brassica genus is complicated, as many of these species are able to cross pollinate naturally. Thus, there is a large amount of genetic variation available to oilseed Brassica breeders. The oilseed brassica species, *B. napus*, *B. rapa*, and *B. juncea* are closely related to one another, as well as to *B. nigra*, *B. oleracea*, and *B. carinata*. Cytological evidence indicates these species all originate from an extinct common ancestor which had 5 or 6 chromosomes, and that the high chromosome number Brassica species (*B. napus, B. juncea*, and *B. carinata*) originated as amphidiploid hybrids from combinations of low chromosome number species (*B. nigra, B. rapa*, and *B. oleracea*). The knowledge of the . relationship between the various Brassica species creates possibilities for producing new synthetic oilseed Brassica material, as well as for transferring traits between the various related Brassica species.

Seedcoat color in rapeseed may be different depending on the particular species and variety of Brassica. Coat color is generally divided into two main classes, yellow or black (or dark brown), although varying shades of these colors, such as reddish brown and yellowish brown are also observed. Seeds with yellow coats have been found to have thinner hulls and thus less fiber and more oil and protein than varieties with dark color seed coats. Yellow-seeded rapeseed varieties are common in Asian countries, and in China, there is an abundance of yellow-seeded cultivars in production rapeseed, particularly in *B. juncea* and *B. rapa* varieties.

In order to improve the nutritional qualities of rapeseed oil, varieties have been developed which contain low erucic acid levels, as well as low glucosinolate levels. These varieties of *B. napus* and *B. rapa* have been termed "canola" by the Canadian breeders involved in their development, and the oils from these varieties are well accepted in the global vegetable oil markets. On the world markets, rapeseed oil does not derive from a particular species, and both high erucic acid and low erucic acid oils contribute to the edible oil supply. In 1996, about 14% of the global edible oil supply was from oilseed Brassica varieties.

The high protein content in its seed meal also makes rapeseed meal a valuable livestock feed, although the relatively high fiber content decreases its digestibility and decreases the value as an animal feed. Also, the presence of glucosinolates can decrease the value of the meal due to the deleterious effects of glucosinolates on growth and reproduction of livestock.

Improved oil and protein levels are primary objectives of rapeseed breeding programs. Thus, introduction of a yellow seed coat trait into canola varieties is desirable, in the interest of providing improvements in both the seed oil and protein levels. Integration of genes controlling seed pigmentation from related Brassica species into valuable oilseed Brassica varieties, such as canola varieties, is complicated by the fact that multiple recessive alleles are involved in the inheritance of yellow seed coats in presently available yellow coat lines.

Accordingly, there is a need in the art for yellow coat oilseed Brassica lines in which the trait for yellow seed coat can be easily transferred to other oilseed Brassica plants, and in particular to canola varieties, these lines can be used to accelerate the development of oilseed Brassica cultivars with improved oil, protein, and fiber contents.

SUMMARY OF THE INVENTION

Rapeseeds and oilseed Brassica plants producing rapeseeds, which have a yellow-seed coat are provided wherein the yellow-seed coat color is controlled by a single locus mutation. The rapeseed is characterized by having high levels of seed oil and protein and low levels of fiber and glucosinolate. The rape plants grown from the seed are also early maturing.

The plants and seed are useful for producing improved canola and rape varieties and for providing a source of valuable meal and oil products.

DETAILED DESCRIPTION OF THE INVENTION

The invention is drawn to rapeseeds which have a yellow-seed coat, as well as to the plants producing such rapeseeds. The yellow-seed coat color is controlled by a single locus mutation. Thus, the trait can be easily transferred to desired lines without the complications associated with multiple gene inheritance.

Yellow seeds have a considerably thinner seed coat than black and brown ones. The thinner seed coat results in a reduced fiber content in the meal and an associated increase in seed oil and protein content as compared with normal levels of oil and protein. In seeds of the invention, seed oil levels are increased at least about 3%, preferably at least about 5%, more preferably at least about 10%.

Yellow-seeded genotypes generally have higher oil and protein concentrations in their seeds. The yellow-coated seeds of the invention display an increase in protein concentration. Protein levels are increased at least about 10%, preferably about 20%, more preferably about 30%.

Yellow-seeded genotypes typically show a decrease in fiber content. The yellow-coated seeds of the invention have decreased fiber content of at least about 2%, preferably about 5%, more preferably about 8%.

The seeds of the invention also exhibit a decrease in glucosinolate levels. Glucosinolate levels are decreased at least about 10%, preferably about 15%, more preferably about 20%. This reduction is important for utilizing the seed mean as animal feed.

Plants from the rapeseeds of the invention mature earlier than the parent lines from which these plants were developed. Earlier maturing varieties are particularly useful. For example, they find use where a short growing season is needed to avoid an environmental stress such as cold or drought or alternatively where multiple crops are grown. Various multiple cropping sequences are needed, particularly in China and India. In Western Canada, B. campestris varieties maturing in less than 100 days are required to escape frost damage. Additionally, short-duration rapeseed varieties are needed in Southern Australian to avoid late-season drought stress. By early maturing is intended that the plants mature at least about 2 days, preferably at least about 5 days, more preferably at least about a week or more early as compared to the parent lines from which the earlier maturing plant lines were developed.

Methods are available in the art for the production of plants and rapeseed of the invention. Generally, plant cells can be mutagenized and selected for those exhibiting the desired trait. Alternatively, the trait can be crossed into desired varieties using standard genetic methods known in the art.

For purposes of the invention, for mutagenesis and selection, plant cells are selected that are capable of regeneration such as seeds, microspores, ovules, pollen, vegetative parts, particularly microspores. For the most part, such plant cells can be selected from any variety of Brassicas, particularly those brassicas having desired agronomic traits.

Generally, methods are available in the art for the preparation of plant cells for mutagenesis. For collection of microspores for use in the invention, inflorescences are obtained from young plants and microspores collected. Microspore culture is an in vitro process whereby immature pollen grains (microspores) are mechanically isolated from anther tissue and are J induced to develop directly into embryos rather than into mature pollen grains. The embryos originating from microspores have only one parental chromosome complement per cell. These embryos can be germinated and grown into plants. Generally, approximately 15–20% of the resulting plants are diploidized, i.e., are dihaploid-plants.

In oilseed brassicas, methods are known in the art for obtaining haploids through anther/microspore culture. See, for example, *Plant Cell Culture in Crop Improvement* edited by Giles and Sen, Plenum, N.Y. (1982); Kameya and Hinata (1970) *Jpn J Breed* 20:82–87; Thomas and Wenzel (1975); Mathias, R (1988) *Plant Breed* 100:320–322; and George et al. (1987) 72–74, herein incorporated by reference. In Brassica, the developmental pathway for haploid induction normally involves the induction of microspore embryogenesis. See, Kott et al. (1988) *Can J Bot* 66:1665–1670. The use of microspore-derived haploids results in a substantial reduction in the time required to develop new varieties. Once the microspore or cell of interest has been obtained, methods are available in the art for mutagenesis. Such methods include radiation, chemical mutagenesis, or a combination of chemical and physical mutagenesis. Mutagenesis is carried out for a duration of time to accomplish genetic modifications, but not so long so as to destroy the viability of the cells and their ability to be regenerated into a plant.

Such modifications can be induced by physical mutagenesis such as radiation. Radiation mutagenesis includes mutagenesis carried out by use of physical means such as x-ray, gamma radiation, ultraviolet radiation, ionizing radiation, and the like. Gamma radiation may be supplied to the plant cells in a dosage of approximately 50 to 200 Krad., preferably from about 60 to about 90 Krad.

Chemical mutagenic agents include ethylmethylsulfonate (EMS), ethylnitrosourea (ENS), 2-aminopurine, 5-bromouracil (5-BU), alkylating agents, etc. Chemical mutagenesis involves the treatment of the cells with a dilute solution of the mutagen, typically about 0.01% to about 10% solution. For example, for the mutagenesis of microspores, a solution of about 0.01% to about 5%, preferably about 0.02% ethylmethylsulfonate is utilized. The microspores are treated with the chemical mutagen for one to several hours, typically about 2 to 3 hours.

The mutations may result in relatively small or even great changes in gene action. Ultimately, gene mutation is a physiochemical event that has the effect of increasing the number of different forms of the gene present in the population.

Haploid plants, mutagenized cells or microspores can be chemically treated to double the chromosome number. Such chemicals include colchicine which prevents the duplicated chromosomes from segregating by blocking spindle-fiber formation. While treatment time may vary, a time of one to several hours, preferably two to three hours is generally sufficient.

Development of homozygous lines by conventional methods involves repeated selfing and selection for several generations within a population. Early generation selection is limited by the heterozygosity of the material handled. Haploidization followed by chromosome doubling of early generation material can expedite the approach and shorten the breeding cycle. Thus, doubled haploid plants are useful for immediately obtaining homogenous plants.

Rape plants are regenerated from the treated cells using known techniques. See, McCormick et al. (1986) *Plant Cell Reports*, 5:81–84. The resulting rapeseeds may be planted in accordance with conventional growing a procedures and following self-pollination rapeseed is formed.

Seed color character is generally scored on healthy plants at or near complete seed maturity. Since seed color in Brassica is determined by the genotype of maternal tissue, i.e., the testa, all $F_1$ seeds of the Brassica plants of the present invention exhibit the same color as the female parent. Thus, when crossing the plants of the present invention to other varieties the successive $F_3$ generation must be analyzed as the yellow coat color is recessive and the seed coat color is determined by the female parent. That is, the seed coat color in the progeny represents the genetic make up of the parent plants. Typically for a single locus trait, the $F_3$ generation must be analyzed to select for those hybrids inheriting the yellow-seed coat trait. In a cross, $F_1$ seed would be all black or yellow depending on whether the yellow seed coat variety was the male or female parent. $F_2$ seed would be all black reflecting the heterozygous nature of the $F_1$ plants. A segregation ratio of 3:1 in the $F_3$ generation (black:yellow) is indicative of a single locus trait.

Care is taken in the growth and maintenance of the treated rapeseed. Particularly, pollination is carefully controlled and monitored. The resulting rapeseed is harvested and subjected to analysis, for seed coat color, fatty acid composition, protein composition, and the like.

Once a plant has been selected exhibiting the yellow coat color, the plant and seed can additionally be tested for other desirable characteristics. Thus, the seed oil can be analyzed for altered fatty acid content, rate of maturity, protein and fiber levels, and the like. For determination of the fatty acid composition of a given rapeseed, methods are available in the art for removal of the oil from the rapeseed and determination of the composition of the oil. Generally, the oil is removed from the rapeseeds by crushing the seeds and extraction of the oil. Nuclear magnetic resonance (NMR), gas liquid chromatography using a capillary column, and near infrared (NIR) spectroscopy can be used to measure the oil content. Generally, the oil is extracted as fatty acid methyl esters following reaction with methanol and sodium hydroxide. The resulting ester can be analyzed for fatty acid content. See, Daun et al. (1983), *J. Amer. Oil. Chem. Soc.* 60:1751–1754; *Oil Crops of the World*, edited by Robbelen et al., Toronto: McGraw-Hill (1989); and Starr et al. (1985) *J Agric Sci Camb* 104:317–323.

*Brassica napus* and *Brassica campestris* are dicotyledonous plants. Thus, the analysis for fatty acid composition may be carried out on a single outer cotyledon and the remaining halfseed can be retained for possible future germination. Methods are available in the art for the separation of the rapeseeds and the two halfseed.

After analysis of the fatty acid composition and seed coat color, seed are selected for further self pollination to achieve substantial genetic homogeneity. Such plants can then be used as breeding or other source material for the production of improved rape varieties.

Improved oil and protein concentrations are primary objectives in rapeseed breeding. Oil and protein levels can be further improved by crossing the plants of the invention with lines which have high oil and protein levels. Likewise, other characteristics may be improved by careful consideration of the parent plant.

Prior to the present application, light seed color has been associated with recessive genes at multiple loci. However, the present invention indicates that a yellow-seed coat rapeseed can be produced wherein the yellow-seed coat is controlled at a single locus.

The discovery of a single locus which is capable of conferring yellow seed color is beneficial for crossing such trait into other rape or canola lines, including high erucic acid lines, canola lines, and other elite lines or rape. The trait can be readily transferred into other plants within the same species by conventional plant breeding techniques including cross-pollination and selection of the progeny. Also, the desired traits can be transferred between species using the same convention plant breeding techniques involving pollen transfer and selection. See, for example, *Brassica crops and wild allies biology and breeding*, edited by S. Tsunada et al., *Japan Scientific Press*, Tokyo (1980); *Physiological Potentials for Yield Improvement of Annual Oil and Protein Crops*, edited by Diepenbrock and Becker, Blackwell Wissenschafts-Verlag Berlin, Vienna (1995); *Canola and Rapeseed*, edited by F. Shahidi, Van Nostrand Reinhold, N.Y. (1990); and *Breeding Oilseed Brassicas*, edited by Labana et al., Narosa Publishing House, New Dehli (1993), herein incorporated by reference.

The yellow seed coat color trait can be readily transferred into other plants within the same Brassica napus or Brassica campestris species by conventional plant breeding techniques. Such techniques include cross-pollination and selection of the progeny. Such techniques can likewise be used to transfer the trait between the napus and campestris species. See, for example, *Brassica Crops and Wild Allies Biology and Breeding*, edited by S. Tsunada et al. *Japan Scientific Press*, Tokyo (1980). Commercially available campestris varieties include Tobin, Horizon, Colt, etc. Following the interspecific cross, members of the $F_1$ generation are self-pollinated to produce $F_2$ seed. Backcrossing is then conducted to obtain a euploid (n=10) campestris line exhibiting the desired trait. Additionally, protoplast fusion and nuclear transplant methods can be used to transfer the trait from one species to another. See, generally, "Fusion of Higher Plant Protoplasts" by Albert W. Ruesink, *Methods in Enzymology*, Vol. LVIII, Jakoby and Pastan. (eds). Academic Press, Inc., New York, N.Y. (1979), and the references cited therein; and Carlson et al. (1972), *Proc. Natl. Acad Sci. USA* 69:2292.

In accordance with the present invention, a substantially uniform assemblage of rapeseed can be produced. Such seed can be used to produce a substantially uniform field of rape plants.

The relatively high content and quality of rapeseed protein make the seed a valuable raw material, not only for the oil industry but also for the feed industry. The factor most limiting utilization of rapeseed meal is the presence of gluscosinolates or the products formed by their cleavage. These compounds are responsible for the enlargement of thyroid glands and hemorrhagic liver syndrome in animals. These affects have limited the use of rapeseed meal, prompting efforts to breed new rapeseed varieties low in gluscosinolates.

Generally, the high fiber content of rapeseed meal contributes to the overall reduction of the feed value of the rapeseed meal. Furthermore, when edible protein products are made from rapeseed meal the dark color of black seed is a considerable problem. The black-seed coat gives an unpleasant grey color to protein products made from rapeseed meal. Therefore the reduction in seed coat color of the rapeseed of the invention is of interest from the point of view of protein quality as well as lecithin quality.

Methods are available for determination of the protein content of the seed. Traditionally, protein content has been determined by the Kjeldahl or micro Kjeldahl approach of acid digestion followed by steam distillation of the liberated nitrogen as ammonia, and back titration. Automated approaches are available using Kjel Foss or the Technicon autoanalyzer. NIR spectroscopy may also be utilized. See, for example, Gehrke et al. (1968) Technicon Symposium, *Automation in Analytical Chemistry* 1:239–251; Williams (1975) *Serial Chem.* 52:561–576; Thachuk, R. (1981) *J. Am. Oil Chem. Soc.* 58:819–822; Starr et al. (1985) *J. Agric. Sci. Camb.* 104:317–323; and *Canola and Rapeseed*, edited F. Shahidi, Van Nostrand Reinhold, New Yoek, 1990, and the references cited therein.

In a particular embodiment of the invention, an improved rapeseed designated LFDF is disclosed. The rapeseed has yellow-seed coat wherein the seed coat color is controlled by a single locus. The locus has been designated LFDF. Seed has been deposited with the American Type Culture Collection and given accession number ATCC 97875. The rapeseed exhibits high levels of seed oil and protein, and low levels of glucosinolate and fiber. Oil extracted from seeds can be analyzed for lines which contain an oil of interest. Plants from the seed mature early. Generally, the plants mature at least 2 days earlier than the cultivars from which they are derived.

The seed and plants therefrom are useful for transferring the yellow-seed coat color into other rape lines, including high erucic acid lines, canola lines, and other elite lines. The plants are useful for the development of cultivars with improved oil, protein, and fiber concentrations.

The following examples are offered by way of illustration and not by way of limitation.

EXPERIMENTAL

Canola microspores from spring line 212/86 may be obtained as follows. Plants are grown at 18° C. days and 13° C. nights and inflorescences are collected when relatively young. Unopened buds less than 0.5 cm in length are selected and surface-sterilized for 20–25 minutes in a 1% sodium hypochlorite solution. The buds are then washed 2–3 times with distilled water to eliminate the hypochlorite and crushed in 5 ml of basic B5 (Gamborg et al. (1968) *Exp. Cell Res.* 50:151) medium containing 13% sucrose ("washing medium") using a mortar and pestle. The resulting paste is filtered through a 50 $\mu$m nylon mesh into a centrifuge tube. The mixture is centrifuged at 1000 rpm for approximately 4 minutes. The pellet is washed twice with washing medium and resuspended in NLN medium (Lichter, R. (1981) *Z. Pflanzenphysiol Bd.* 103:229–237). The cell density is determined using a hemocytometer and adjusted to 200,000 microspores/ml, and microspores are distributed in 7–10 ml aliquots in 9 cm petri dishes and incubated for 24 hours at 32° C. The microspores are then mutagenized by treatment with 0.02% ethylmethylsulfonate (EMS) for 2½ hours followed by centrifugation at 1000 rpm and two washings in fresh NLN medium.

A colchicine treatment (2 hours with 0.15% colchicine) may be added at this stage for a portion of the microspores for the induction of diploidization of the dividing microspores at an early stage. The colchicine treatment is followed by additional rounds of centrifugation and washing in NLN medium, and the density of the microspores adjusted to 50,000–100,000/ml. The microspores are incubated an additional 24 hours at 32° C. The dividing microspore cultures are incubated at 25–27° C. and embryos are visible after 7–10 days. The embryos are incubated for an additional 10–15 days at 27° C. at which point they can be easily manipulated.

Embryos are cultured to induce shoot regeneration as follows. The embryo root tip is removed by cutting and embryo is placed on B5 plus BAP2 (2 mg/l benzylaminopurine) media plates (10/plate) for 7–10 days. Emerging shoots are collected from the embryos and transferred to magenta boxes (5 shoots per box) containing B5+2IBA (2 mg/l isobutyric acid) medium. When the rooted plantlets are approximately 1 cm in height, they are incubated in a colchicine bath for approximately 2 hours to induce diploidization of the haploid embryos. The plantlets are then removed from the colchicine bath, and transferred to soil for growth into mature plants.

Mature seeds which developed on mutant E25–59 plants were observed to have a yellow seed coat. Dihaploid seeds of E25–59 were grown to increase the available seed for analysis. Pooled seed samples from the resulting plants were analyzed to determine fatty acid composition, and protein, oil, fiber and glucosinolate contents. Oil and protein contents were increased in E25–59 seeds as compared to seeds from 212/86 control plants, whereas fiber and glucosinolate contents were decreased.

Oil levels of approximately 37% were observed in dihaploid E25–59 seeds, representing an increase of 3 percentage units over the 34% oil levels determined for control 212/86 seeds. This represents an approximately 9% increase in oil levels. Protein content in dihaploid E25–59 seeds was measured and an increase was observed over the levels of control seeds. Fiber content in dihaploid E25–59 seeds was measured at 9.8%, 3.3 percentage units lower than the 13.1% levels measured in control 212/86 seeds, or an approximately 25% reduction in fiber content. Glucosinolate content in dihaploid E25–59 seeds was measured at approximately 5.2 $\mu$mole/g defatted germ as compared to a content of 6.0 $\mu$mole/g defatted germ in control 212/86 seeds, a decrease of approximately 0.8 $\mu$mole/g, or 13%.

To test the inheritance pattern of the yellow coat trait, the E25–59 mutant was crossed with canola varieties Cyclone and Hyola and several experimental B napus lines and the segregation patterns determined. F1 seed resulting from the crosses is all yellow when E25–59 is the female parent in the cross or all the normal black color of canola seed if E25–59 is the male parent. This reflects the maternal pattern of inheritance for the yellow coat trait. F2 seed in all crosses is black reflecting that the plants are heterozygous for the recessive yellow coat trait. F3 seeds are analyzed to determine segregation ratios and results are shown in Table 1 below.

TABLE 1

| Cross | # Yellow coat/# Plants |
|---|---|
| B25-59 × Cyclone | 22/100 |
| B25-59 × E25-39 | 18/78 |
| E25-39 × E25-59 | 23/88 |
| E25-59 × Hyola | 63/300 |
| E25-59 × 93FG45 | 24/100 |
| Q30-200 × E25-59 | 14/86 |
| E25-59 × Q30-200 | 8/46 |
|  | 172/798 |

The above results indicate a 3:1 segregation ration for the yellow coat trait, evidence that a single recessive locus mutation, now termed LFDF, is responsible for the trait.

Field observations of the E25–59 line indicate that the yellow seed coat mutation also contributes to early maturing of the mutant seeds. E25–59 seed is mature approximately one week earlier than are seeds from non-mutagenized 212/86, a particularly "late" Canola variety.

The novel properties resulting from the LFDF mutation were verified in analyses of segregating F3 hybrid seeds resulting from the above crosses. Oil content analyses of the hybrid seeds is provided in Table 2 below.

TABLE 2

| Hybrid over Black Coat | Oil Content Range (%) | Average | Average Percentage Units Increase | Average Oil Increase |
|---|---|---|---|---|
| E25-59 × 212/86 | | | | |
| Black Coat | 36.2–42.6 | 39.9 | | |
| Yellow Coat | 37.1–46.3 | 42.5 | 2.6% | 6.5% |
| E25-59 × Cyclone | | | | |
| Black Coat | 37.3–41.7 | 39.5 | | |
| Yellow Coat | 387.7–45.5 | 43.2 | 3.7% | 9.4% |
| E25-59 × Hyola | | | | |
| Black Coat | 35.2–44.0 | 40.4 | | |
| Yellow Coat | 39.5–46.2 | 42.7 | 2.3% | 5.7% |

The above data confirm that the oil contents between black coated and yellow coated hybrids are significantly different according to "student t" test analysis and that the oil content is higher in yellow coated seeds. Genetic background is noted to effect the yellow coat trait, and the trait is observed to have the greatest effect in seeds resulting from the E25–59 X Cyclone cross. The range of oils obtained demonstrates the potential to obtain even higher oil contents, depending on the genetic contribution of the hybrid parents.

Glucosinolate levels are also decreased in the hybrid seeds. For example, average glucosinolate levels in E25–59 X Cyclone were 3.72 μmoles/gram fresh weight, as compared to levels of 4.36 in Cyclone.

Earliness is also observed in the LFDF hybrid plants. Seeds from a yellow coat E25–59 X Cyclone line mature approximately 5 days earlier than do Cyclone seeds.

The rapeseeds and methods of the present invention can be utilized to develop yellow seeded coated varieties of rapeseed. These varieties are desired because light-pigmented genotypes have higher oil and protein concentrations in their seeds than dark seeded genotypes. The present invention has isolated a yellow-seed coat line where yellow-seed coat can be controlled by a single locus. Accordingly, the mutant line and progeny thereof can be utilized in breeding and hybridization to transfer the trait into desired lines of Brassica.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Many modifications and other embodiments of the invention will come to mind in one skilled in the art to which this invention pertains having the benefit of the teachings presented in the foregoing descriptions and the associated drawings. Therefore, it is to be understood that the invention is not to be limited to the specific embodiments disclosed. Although specific terms are employed, they are used in a generic and descriptive sense only and not for purposes of limitation, and that modifications and embodiments are intended to be included within the scope of the appended claims.

That which is claimed:

1. An oil composition that comprises oil derived from a seed from either a *Brassica napus* or a *Brassica rapa* plant bearing a mutation, wherein said mutation is in a locus designated as LFDF in E25–59 (deposited at ATCC Deposit Number 97875), wherein said seed has a yellow seed coat, and wherein said mutation is a recessive single locus mutation that contributes to the color of said seed coat.

2. The oil composition of claim 1, wherein said seed has an increased level of seed oil as compared to seed oil level in a non-yellow seed parent line.

3. The oil composition of claim 1, wherein said seed has an increased level of seed protein as compared to seed protein level in a non-yellow seed parent line.

4. The oil composition of claim 1, wherein said seed has a decreased level of seed fiber as compared to seed fiber level in a non-yellow seed parent line.

5. The oil composition of claim 1, wherein said seed has a decreased level of seed glucosinolates as compared to seed glucosinolates level in a non-yellow seed parent line.

6. The oil composition of claim 1, wherein a plant grown from said seed matures at least 2 days early as compared to a second plant grown from seed from a non-yellow seed parent line from which said *Brassica Naples* or *Brassica rapa* plant is derived.

7. The oil composition of claim 1, wherein said *Brassica napus* or *Brassica rapa* plant is a canola plant.

8. The oil composition of claim 1, wherein said *Brassica napus* or *Brassica rapa* plant is a high erucic acid rapeseed plant.

9. The oil composition of claim 1, wherein said mutation is also found in E25–59.

10. An oil composition that comprises oil derived from a *Brassica napus* seed having a mutation, wherein said mutation is in a locus designated as LFDF in E25–59 (deposited as ATCC Deposit Number 97875), wherein hybrids homozygous for said mutation have a yellow seed coat, and wherein said yellow seed coat phenotype segregates with a pattern indicating that said mutation acts as a single recessive mutation.

11. The oil composition of claim 10, wherein said seed has an increased level of seed oil as compared to seed oil level in a non-yellow seed parent line.

12. The oil composition of claim 10, wherein said seed has an increased level of seed protein as compared to seed protein level in a non-yellow seed parent line.

13. The oil composition of claim 10, wherein said seed has a decreased level of seed fiber as compared to seed fiber level in a non-yellow seed parent line.

14. The oil composition of claim 10, wherein said seed has a decreased level of seed glucosinolates as compared to seed glucosinolates level in a non-yellow seed parent line.

15. The oil composition of claim 10, wherein a plant grown from said seed matures at least 2 days early as compared to a second plant grown from seed from a non-yellow seed parent line from which said *Brassica napus* seed is derived.

16. The oil composition of claim 10, wherein said mutation is also found in E25–59.

17. An oil composition that comprises oil derived from a *Brassica napus* plant or seed bearing a mutation in one or more alleles of a locus, wherein the locus is designated as LFDF in E25–59 (deposited as ATCC Deposit Number 97875), wherein said mutation is also found at the LFDF locus in E25–59.

18. The oil composition of claim 17, wherein said seed has an increased level of seed oil as compared to seed oil level in a non-yellow seed parent line.

19. The oil composition of claim 17, wherein said seed has an increased level of seed protein as compared to seed protein level in a non-yellow seed parent line.

20. The oil composition of claim 17, wherein said seed has a decreased level of seed fiber as compared to seed fiber level in a non-yellow seed parent line.

21. The oil composition of claim 17, wherein said seed has a decreased level of seed glucosinolates as compared to seed glucosinolates level in a non-yellow seed parent line.

22. The oil composition of claim 17, wherein a plant grown from said seed matures at least 2 days early as compared to a second plant grown from seed from a non-yellow seed parent line from which said *Brassica napus* plant or seed is derived.

23. An oil composition that comprises oil derived from a *Brassica rapa* plant or seed having a mutation, wherein said mutation is in a locus designated as LFDF in E25–59 (deposited as ATCC Deposit Number 97875), wherein hybrids homozygous for said mutation have a yellow seed coat, and wherein said yellow seed coat phenotype segregates with a pattern indicating that said mutation acts as a single recessive mutation.

24. The oil composition of claim 23, wherein said seed has an increased level of seed oil as compared to seed oil level in a non-yellow seed parent line.

25. The oil composition of claim 23, wherein said seed has an increased level of seed protein as compared to seed protein level in a non-yellow seed parent line.

26. The oil composition of claim 23, wherein said seed has a decreased level of seed fiber as compared to seed fiber level in a non-yellow seed parent line.

27. The oil composition of claim 23, wherein said seed has a decreased level of seed glucosinolates as compared to seed glucosinolates level in a non-yellow seed parent line.

28. The oil composition of claim 23, wherein a plant grown from said seed matures at least 2 days early as compared to a second plant grown from seed from a non-yellow seed parent line from which said *Brassica rapa* plant or seed is derived.

29. The oil composition of claim 23, wherein said mutation is also found in E25–59.

30. An oil composition that comprises oil derived from a *Brassica rapa* plant which produces a seed, wherein said seed has a yellow seed coat, and wherein the single locus mutation designated LFDF in E25–59 (deposited as ATCC Deposit Number 97875), contributes to the color of said seed coat.

31. The oil composition of claim 30, wherein said seed has an increased level of seed oil as compared to seed oil level in a non-yellow seed parent line.

32. The oil composition of claim 30, wherein said seed has an increased level of seed protein as compared to seed protein level in a non-yellow seed parent line.

33. The oil composition of claim 30, wherein said seed has a decreased level of seed fiber as compared to seed fiber level in a non-yellow seed parent line.

34. The oil composition of claim 30, wherein said seed has a decreased level of seed glucosinolates as compared to seed glucosinolates level in a non-yellow seed parent line.

35. The oil composition of claim 30, wherein a plant grown from said seed matures at least 2 days early as compared to a second plant grown from seed from a non-yellow seed parent line from which said *Brassica rapa* plant is derived.

36. The oil composition of claim 30, wherein said mutation is also found in E25–59.

37. Meal derived from a seed from either a *Brassica napus* or a *Brassica rapa* plant bearing a mutation, wherein said mutation is in the locus designated as LFDF in E25–59 (deposited at ATCC Deposit Number 97875), wherein said seed has a yellow seed coat, and wherein said mutation is a recessive single locus mutation that contributes to the color of said seed coat.

38. The meal of claim 37, wherein said seed has an increased level of seed oil as compared to seed oil level in a non-yellow seed parent line.

39. The meal of claim 37, wherein said seed has an increased level of seed protein as compared to seed protein level in a non-yellow seed parent line.

40. The meal of claim 37, wherein said seed has a decreased level of seed fiber as compared to seed fiber level in a non-yellow seed parent line.

41. The meal of claim 37, wherein said seed has a decreased level of seed glucosinolates as compared to seed glucosinolates level in a non-yellow seed parent line.

42. The meal of claim 37, wherein a plant grown from said seed matures at least 2 days early as compared to a second plant grown from seed from a non-yellow seed parent line from which said *Brassica napus* or *Brassica rapa* plant is derived.

43. The meal of claim 37, wherein said *Brassica napus* or *Brassica rapa* plant is a canola plant.

44. The meal of claim 37, wherein said *Brassica napus* or *Brassica rapa* plant is a high erucic acid rapeseed plant.

45. The meal of claim 37, wherein said mutation is also found in E25–59.

46. Meal derived from a *Brassica napus* plant or seed having a mutation, wherein said mutation is in a locus designated as LFDF in E25–59 (deposited as ATCC Deposit Number 97875), wherein hybrids homozygous for said mutation have a yellow seed coat, and wherein said yellow seed coat phenotype segregates with a pattern indicating that said mutation acts as a single recessive mutation.

47. The meal of claim 46, wherein said seed has an increased level of seed oil as compared to seed oil level in a non-yellow seed parent line.

48. The meal of claim 46, wherein said seed has an increased level of seed protein as compared to seed protein level in a non-yellow seed parent line.

49. The meal of claim 46, wherein said seed has a decreased level of seed fiber as compared to seed fiber level in a non-yellow seed parent line.

50. The meal of claim 46, wherein said seed has a decreased level of seed glucosinolates as compared to seed glucosinolates level in a non-yellow seed parent line.

51. The meal of claim 46, wherein a plant grown from said seed matures at least 2 days early as compared to a second plant grown from seed from a non-yellow seed parent line from which said *Brassica napus* plant or seed is derived.

52. The meal of claim 46, wherein said mutation is also found in E25–59.

53. Meal derived from a *Brassica napus* or a *Brassica rapa* plant or seed bearing a mutation in one or more alleles of a locus, wherein the locus is designated as LFDF in E25–59 (deposited as ATCC Deposit Number 97875), wherein said mutation is also found at the LFDF locus in E25–59.

54. The meal of claim 53, wherein said seed has an increased level of seed oil as compared to seed oil level in a non-yellow seed parent line.

55. The meal of claim 53, wherein said seed has an increased level of seed protein as compared to seed protein level in a non-yellow seed parent line.

56. The meal of claim 53, wherein said seed has a decreased level of seed fiber as compared to seed fiber level in a non-yellow seed parent line.

57. The meal of claim 53, wherein said seed has a decreased level of seed glucosinolates as compared to seed glucosinolates level in a non-yellow seed parent line.

58. The meal of claim 53, wherein a plant grown from said seed matures at least 2 days early as compared to a second plant grown from seed from a non-yellow seed parent line from which said *Brassica napus* or *Brassica rapa* plant or seed is derived.

59. Meal derived from a *Brassica rapa* plant or seed having a mutation, wherein said mutation is in a locus designated as LFDF in E25–59 (deposited as ATCC Deposit Number 97875), wherein hybrids homozygous for said mutation have a yellow seed coat, and wherein said yellow seed coat phenotype segregates with a pattern indicating that said mutation acts as a single recessive mutation.

60. The meal of claim 59, wherein said seed has an increased level of seed oil as compared to seed oil level in a non-yellow seed parent line.

61. The meal of claim 59, wherein said seed has an increased level of seed protein as compared to seed protein level in a non-yellow seed parent line.

62. The meal of claim 59, wherein said seed has a decreased level of seed fiber as compared to seed fiber level in a non-yellow seed parent line.

63. The meal of claim 59, wherein said seed has a decreased level of seed glucosinolates as compared to seed glucosinolates level in a non-yellow seed parent line.

64. The meal of claim 59, wherein a plant grown from said seed matures at least 2 days early as compared to a second plant grown from seed from a non-yellow seed parent line which said *Brassica rapa* plant or seed is derived.

65. The meal of claim 59, wherein said mutation is also found in E25–59.

66. Meal derived from a *Brassica napus* or a *Brassica rapa* plant, which produces seeds, wherein said seeds have a yellow seed coat, and wherein the single locus mutation designated LFDF in E25–59 (deposited as ATCC Deposit Number 97875), contributes to the color of said seed coat.

67. The meal of claim 66, wherein said seed has an increased level of seed oil as compared to seed oil level in a non-yellow seed parent line.

68. The meal of claim 66, wherein said seed has an increased level of seed protein as compared to seed protein level in a non-yellow seed parent line.

69. The meal of claim 66, wherein said seed has a decreased level of seed fiber as compared to seed fiber level in a non-yellow seed parent line.

70. The meal of claim 66, wherein said seed has a decreased level of seed glucosinolates as compared to seed glucosinolates level in a non-yellow seed parent line.

71. The meal of claim 66, wherein a plant grown from said seed matures at least 2 days early as compared to a second plant grown from seed from a non-yellow seed parent line from which said *Brassica napus* or *Brassica rapa* plant is derived.

72. The meal of claim 66, wherein said mutation is also found in E25–59.

* * * * *